United States Patent [19]

Matuda et al.

[11] Patent Number: 5,078,971
[45] Date of Patent: * Jan. 7, 1992

[54] DEODORIZER DEVICE

[75] Inventors: Michiya Matuda; Tooru Kobayashi, both of Tochigi; Fumikazu Washimi, Ashikaga; Masaei Kawashima; Masaaki Kashiwabuchi, both of Tochigi; Kikuzi Takahashi, Ibaraki; Atsushi Kanai, Tochigi, all of Japan

[73] Assignee: Hitachi, Ltd., Tokyo, Japan

[*] Notice: The portion of the term of this patent subsequent to Sep. 11, 2007 has been disclaimed.

[21] Appl. No.: 450,460

[22] Filed: Dec. 14, 1989

[30] Foreign Application Priority Data

Dec. 19, 1988 [JP] Japan ................. 63-318552

[51] Int. Cl.$^5$ ............................................ A61L 9/20
[52] U.S. Cl. .................................... 422/121; 422/122; 422/124; 422/125; 422/306; 502/5; 62/78; 62/264

[58] Field of Search ............... 422/120, 121, 122, 124, 422/125, 306; 62/78, 264; 502/5

[56] References Cited

U.S. PATENT DOCUMENTS

| | | | |
|---|---|---|---|
| 4,904,289 | 2/1990 | Miyakami et al. | 62/78 X |
| 4,948,567 | 8/1990 | Atarashiya | 62/78 X |
| 4,954,465 | 9/1990 | Kawashima et al. | 62/264 X |
| 4,955,208 | 11/1990 | Kawashima et al. | 62/264 |

Primary Examiner—Robert J. Warden
Assistant Examiner—Lyle A. Alexander
Attorney, Agent, or Firm—Antonelli, Terry, Stout & Kraus

[57] ABSTRACT

A deodorizer device for use in a refrigerator has an absorbent capable of absorbing odor components from air, a layer of a photocatalyst deposited on the surface of the absorbent, and a light source for illuminating the photocatalyst layer to excite the same. Air containinig odor components is forced by a blower to flow through the absorbent.

11 Claims, 4 Drawing Sheets

DEODORIZER DEVICE

BACKGROUND OF THE INVENTION

1. Field of the Invention

The present invention relates to a deodorizer device suitable for use in a refrigerator which stores foods and other materials.

2. Description of the Prior Art

A conventional deodorizer device for use in a refrigerator has a case charged with an absorbent such as activated carbon and is placed in the path of chilled air in the refrigerator so as to absorb and remove any smell generated in the refrigerator. A typical example of the deodorization device of this kind is disclosed in, for example, Japanese Unexamined Utility Model Publication No. 47-22566.

As explained above, the conventional deodorization device makes use of an absorbent such as activated carbon. The absorbent tends to reduce its deodorization effect when used in air having a strong smell. There is a practical limit or saturation level in the capacity of the absorbent for holding odor components. Thus, the absorbent has to be demounted from the deodorization device for replacement or regeneration after a predetermined time of use.

SUMMARY OF THE INVENTION

Accordingly, an object of the present invention is to provide a deodorizer device which can maintain the deodorizing ability for a long time without requiring substantial maintenance work.

To this end, according to the present invention, there is provided a deodorizer device comprising: an absorption unit including an odor absorbent capable of absorbing an odor component and a layer of a photocatalyst deposited on a surface of the absorbent and capable of decomposing the odor component absorbed in the absorbent when excited by irradiation with light; a light source for applying the exciting light to the layer of photocatalyst; and a blower which causes air containing the odor component to pass through the absorption unit.

In the deodorization device of the invention, light having an energy of a level not smaller than the band gap energy of the photocatalyst layer is applied to the photocatalyst layer on the absorbent so as to excite the photocatalyst layer. In consequence, the photocatalyst of the catalytic layer is effective to decompose the odor components, so that the odor components in the absorbent are progressively decomposed and removed from the absorbent surface.

When the light source is of a type which does not produce any appreciable heat, the decomposition proceeds in accordance with diffusion of the odor components caused by the difference in the density of the components between the outer and inner portions of the absorbent, so that the decomposition and removal are effected gradually from the surface of the absorbent.

In contrast, when the light source is of a type which produces heat, the temperature of the absorbent is raised to reduce its capacity for holding the odor components, so that the odor components are released from the inner portion of the absorbent, and the thus released odor components are further decomposed by the photocatalyst layer on the surface of the absorbent.

It is, therefore, possible to regenerate the absorbent so that the deodorization device can stably maintain its deodorization effect for a long time.

In a preferred embodiment of the present invention, the deodorization device has suction and discharge chambers which are separated from each other by the absorption unit. This arrangement prevents undesirable mixing of the air before deodorization and the air after deodorization, so that the odor components are effectively trapped by the absorption unit.

According to the preferred embodiment of the invention, a control circuit substrate, a reflective means, an ultraviolet lamp and the absorption unit are arranged in line in the mentioned order so that the absorption unit can be irradiated over its whole surface with the ultraviolet rays.

In the preferred embodiment of the invention, the ultraviolet lamp and a resistor of a stabilizer of the lamp are arranged on both sides of the absorption unit so that the temperature of the absorption unit is raised by the heat from the resistor to promote the exudation of the odor components to the surface of the absorption unit, whereby the decomposition of the odor components is effected at a high efficiency.

In the preferred embodiment of the invention, the control circuit substrate and the resistor of the lamp stabilizer are installed separately from each other so as to enable the substrate to be hermetically sealed.

In the preferred embodiment of the present invention, heat-generating components of the control circuit are disposed on the lower side of the control circuit substrate and in the vicinity of connection terminals. In this arrangement, heat generated by the heat-generating components effectively prevents any trouble due to dew which may form on the terminals when air of high humidity is introduced into contact with these terminals.

In the preferred embodiment of the invention, the deodorizer device is sized to have a height smaller than and approximating the minimum dimension between shelves in the refrigerator chamber. Thus, the deodorizer device can have a reduced length and width so as to minimize the installation space, thereby assuring an efficient use of the space in the refrigerator chamber.

The above and other objects, features and advantages of the present invention will be made more apparent by the following description with reference to the accompanying drawings.

DESCRIPTION OF THE PREFERRED EMBODIMENT

Figure 1:
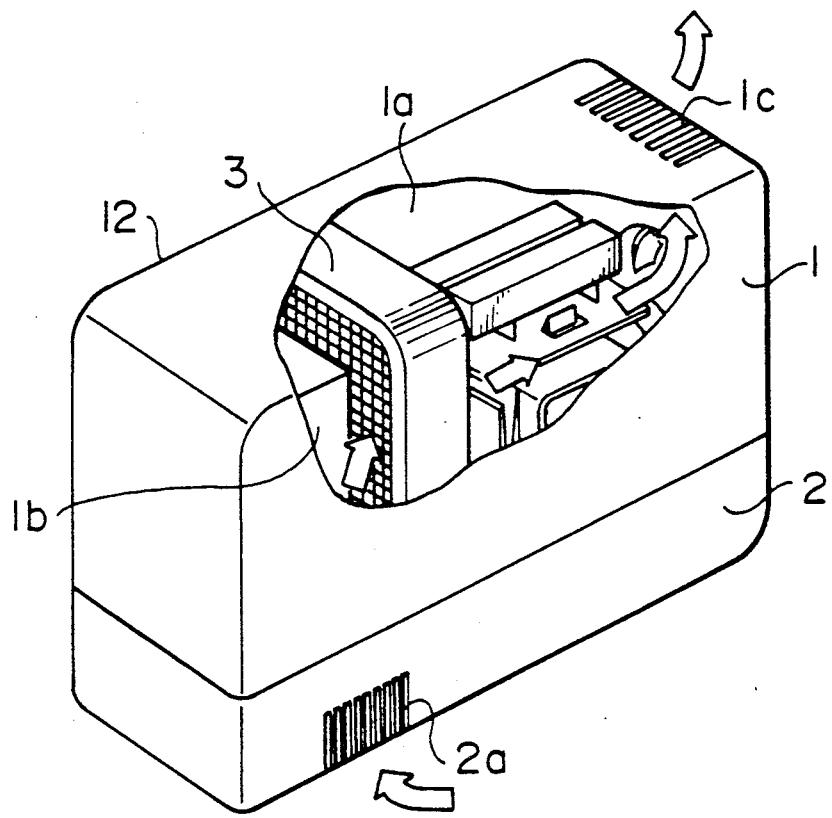
FIG. 1 is a partly cut-away perspective view of an embodiment of a deodorizer device of the present invention.
Figure 2:
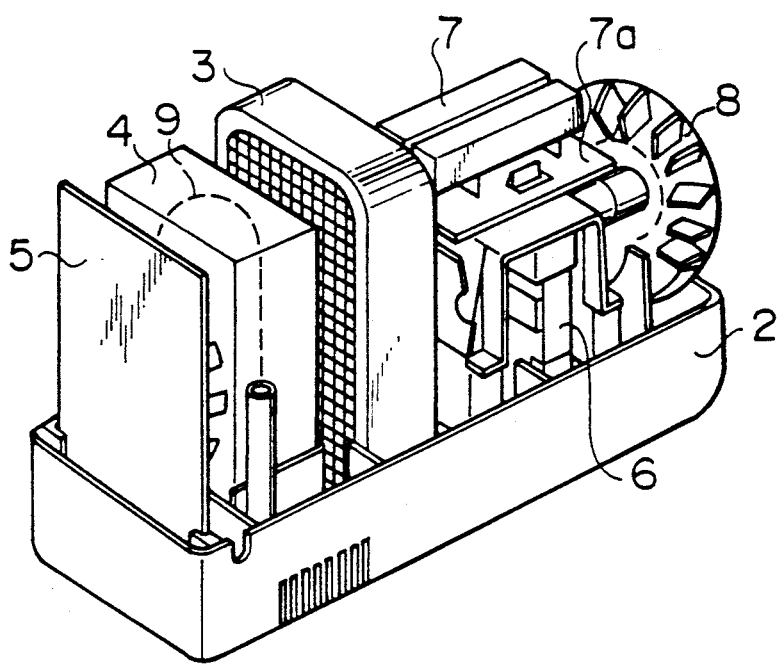
FIG. 2 is a perspective view of the internal structure of the deodorizer device of FIG. 1.

FIG. 1 shows an embodiment of a deodorizer device 12 of the present invention in a perspective view with a part thereof cut and removed. FIG. 2 is a perspective view of the same deodorizer device with a cover 1 of the device removed to show the internal structure.

The deodorizer device 12 of the illustrated embodiment of the invention is designed for use in a refrigerator chamber and includes an odor absorption unit 3 which comprises a honeycomb structure formed of a molded absorbent and a layer of a photocatalyst deposited on the surfaces of the honeycomb structure and adapted to be excited by an ultraviolet ray to decompose the components of odors (hereinafter referred to as "odor components") already absorbed in the honeycomb structure of the absorbent. The deodorizer device 12 further includes an ultraviolet lamp 9 operative to radiate an ultraviolet ray to the photocatalyst layer of the odor absorption unit 3 to excite the photocatalyst. Such a deodorizer device is fully described in U.S. patent application Ser. No. 295,754 filed Jan. 11, 1989, now U.S. Pat. No. 4,954,465 the disclosure of which is incorporated herein by reference.

A metallic cover serving as reflection means 4 is disposed in the vicinity of the ultraviolet lamp 9 so as to direct the ultraviolet ray from the lamp 9 towards the absorption unit 3. The deodorizer device 12 further has a stabilizer resistor 7 for the ultraviolet lamp 9, a support plate 7a supporting the resistor 7, a blower 8 for forcibly causing air containing odor components to pass through the absorption unit 3, a motor 6 for driving the blower 8, and a control circuit substrate 5 carrying thereon an electric control circuit for controlling the operation of the ultraviolet lamp 9 and the operation of the driving motor 6.

As will be seen from FIG. 1, the deodorizer device 12 has upper and lower covers 1 and 2 which cooperate to define a suction chamber 1b and a discharge chamber 1a which are separated from each other by the absorption unit 3. The lower cover 2 is provided with a row of suction openings 2a communicating with the suction chamber 1b, while the upper cover 1 is provided with a row of discharge openings 1c communicating with the discharge chamber 1a. The control circuit substrate 5, the reflection means 4 and the ultraviolet lamp 9 are arranged in series in the mentioned order within the suction chamber 1b. The discharge chamber 1a accommodates the stabilizer resistor 7 for the ultraviolet lamp 9, the support plate 7a for the resistor 7, the blower 8 and the drive motor 6 for driving the blower 8.

Air containing odor components is sucked through the suction openings 2a into the suction chamber 1b. The air is then caused to pass through the absorption unit 3 so that odor components are trapped by the absorption unit 3. The air with a reduced content of the odor components is then discharged from the discharge chamber 1a into the refrigerator chamber through the discharge openings 1c. The ultraviolet ray from the ultraviolet lamp 9 excites the photocatalyst layer on the absorbent of the absorption unit 3 so that the photocatalyst produces an effect to decompose the odor components, whereby the odor components absorbed in the absorbent are progressively decomposed and removed from the surface of the absorbent.

Since the suction chamber 1b and the discharge chamber 1a are isolated from each other by the absorption unit 3, there is no risk that the air after deodorization and the air before deodorization are mixed with each other within the deodorizer device, so that the odor components carried by the air are effectively absorbed by the absorption unit 3.

The reflective means 4 may be formed by a cover of, for example, aluminum and be designed to reflect the ultraviolet ray from the lamp 9 to allow the entire area of the absorption unit 3 to be irradiated with the ray and, at the same time, shield the control circuit substrate 5 from the ultraviolet ray. The stabilizer resistor 7 of the ultraviolet lamp 9 is disposed on the side of the absorption unit 3 opposite to the lamp 9, so that the absorption unit 3 is heated at both of its sides by the heat from the ultraviolet lamp 9 and the heat from the stabilizer resistor 7, whereby exudation of the odor components from the inner portions of the absorbent is promoted to ensure a high efficiency of decomposing action performed by the photocatalyst layer.

The outline of the refrigerator deodorizer device of the present invention has been described. Description will now be made of some details of the embodiment of the invention.

Figure 4:
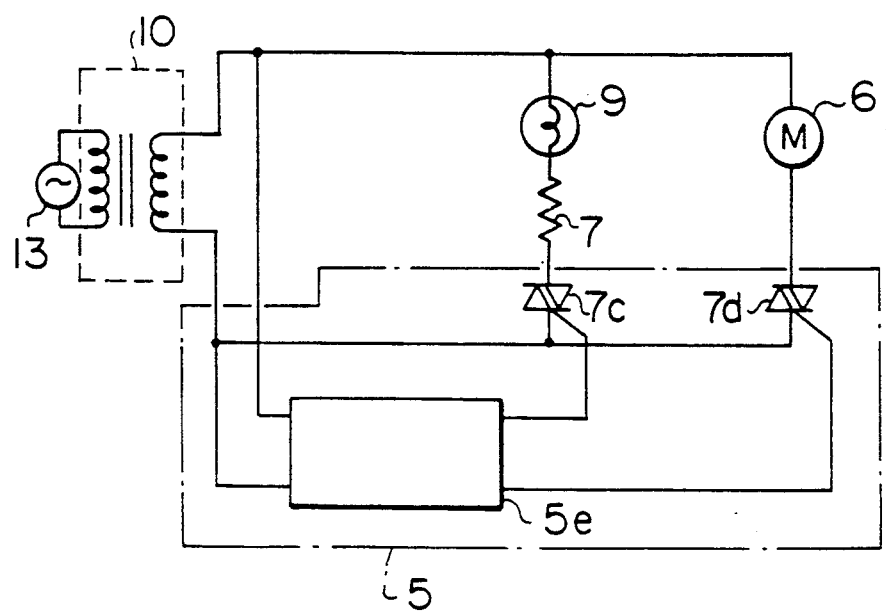
FIG. 4 is a block diagram of an electrical circuit incorporated in the device shown in FIG. 1.

Referring to FIG. 4, there is shown a block diagram of an electrical circuit which can be used in the refrigerator deodorizer device of the present invention.

An electrical circuit 5e, which is carried by the control circuit substrate 5, controls a semiconductor control element 7c for selectively supplying electrical current to the ultraviolet lamp 9 and the stabilizer resistor 7, and a semiconductor control element 7d which selectively supplies electrical current to the driving motor 6 of the blower 8. A power supply 13 supplies a voltage to the electrical circuit 5e of the deodorizer device 12 through a power supply adapter 10 designed to lower the voltage from the power supply 13. This arrangement makes it possible to reduce the size of the stabilizer resistor 7 and, hence, the size of the refrigerator deodorizer device 12. The aforementioned semiconductor control elements 7c and 7d are carried by the substrate 5.

Figure 3:
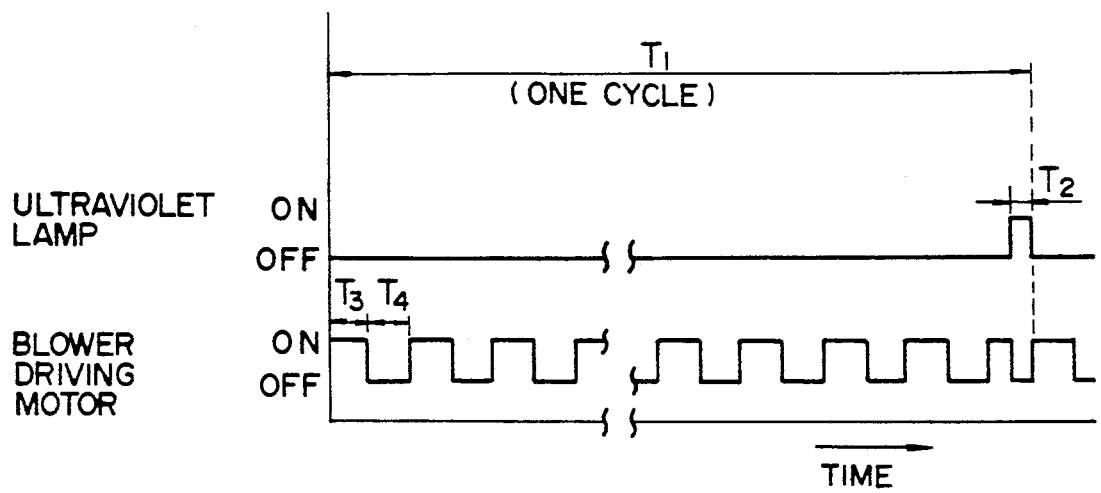
FIG. 3 is a chart illustrative of the operation of a control circuit.

Referring to FIG. 3, there is shown an example of the control of operation of the ultraviolet lamp 9 and the blower driving motor 6 performed by the electrical circuit 5e on the control circuit substrate 5.

The supply of the electrical current to the driving motor 6 is conducted for a period $T_3$ and interrupted for a period $T_4$. The ultraviolet lamp 9 is supplied with a current for a period $T_2$ so that it emits light once in a period $T_1$ of one cycle of operation. The period $T_1$ of one cycle of the operation of the deodorizer device is, for example, 6 to 8 hours. Period $T_2$, $T_3$ and $T_4$ are, for example, 12 minutes, 24 minutes and 24 minutes, respectively.

Figure 5:
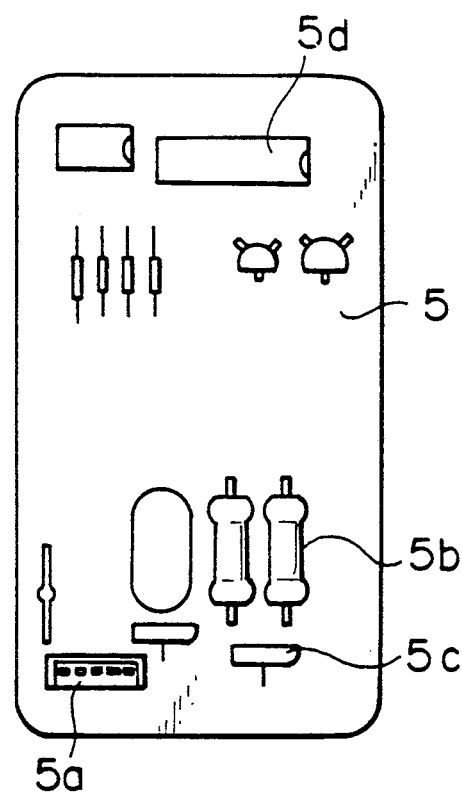
FIG. 5 is a plan view of a control circuit substrate in the device shown in FIG. 1.

FIG. 5 schematically shows component parts of the electrical circuit 5e on the control circuit substrate 5. The electrical circuit 5e has a terminal device 5a for the power supply lines to the driving motor 6 and the ultraviolet lamp 9, a semiconductor switching element 5c, a gate-current limiting resistor 5b, and an integrated control circuit 5d. Heat-generating elements such as the semiconductor switching element 5c and the gate-current limiting resistor 5b are disposed in the vicinity of the terminal device 5a so that the heat produced by these elements effectively prevent an accident which may otherwise be caused by dew forming on the terminal device 5a when air having a high humidity is introduced into contact with the terminal device 5a.

These heat-generating elements may be arranged on the lower side of the control circuit substrate 5 so that the whole control circuit substrate 5 is heated. This arrangement prevents any accident which may otherwise be caused by dew forming on the substrate 5 when it is cooled.

The stabilizer resistor 7, which is comparatively large in size, is installed separately from the control circuit substrate 5. This arrangement makes it possible to hermetically seal the control circuit substrate 5 and the circuit elements carried by the substrate 5, thus preventing any accident which may otherwise be caused by dew forming.

Figure 6:
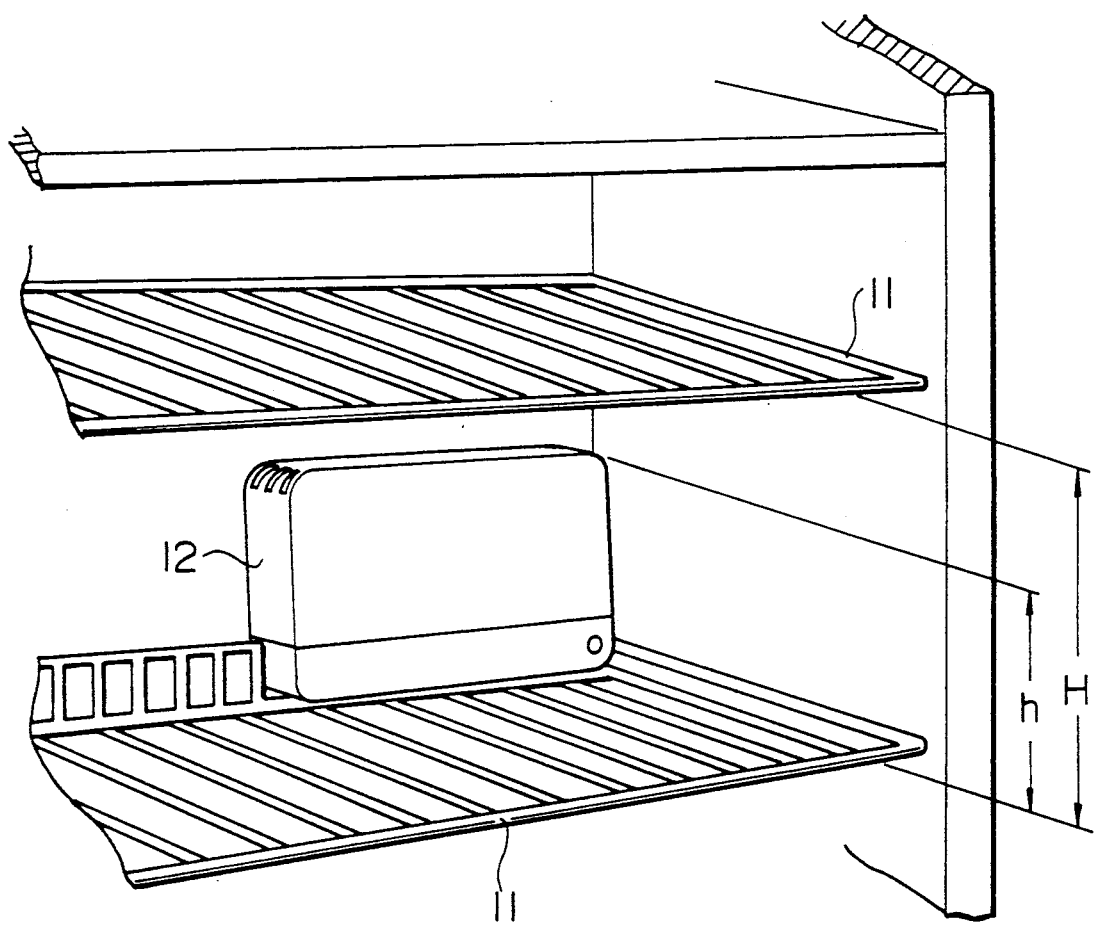
FIG. 6 is a perspective view of the deodorizer installed on a shelf in a refrigerator chamber.

FIG. 6 shows the manner in which the deodorizer device 12 of the present invention is installed in a refrigerator chamber. The deodorizer device 12 has a height h which is slightly smaller than the minimum shelf interval H between shelves 11 in the refrigerator chamber. The minimum shelf interval H is usually 110 mm or greater in ordinary refrigerator chambers, so that the height h of the deodorizer device 12 is determined to be, for example, 100 mm. This design minimizes the length and width of the deodorizer device 12 to allow the space in the refrigerator chamber to be fully utilized.

What is claimed is:

1. A deodorizer device comprising:
   an absorption unit including an odor absorbent capable of absorbing an odor component and a layer of a photocatalyst deposited on a surface of said absorbent and capable of decomposing said odor component absorbed by said absorbent when excited by irradiation with light;
   a light source for irradiates said layer of said photocatalyst with light; and
   a blower which causes air containing the odor component to pass through said absorption unit.

2. A deodorizer device according to claim 1, wherein said light source includes an ultraviolet lamp and reflection means capable of reflecting ultraviolet radiation from said ultraviolet lamp to direct said ultraviolet radiation towards said absorption unit.

3. A deodorizer device according to claim 2, further comprising a control circuit substrate carrying thereon a circuit for controlling operation of said ultraviolet lamp and said blower, said reflection means being arranged to prevent said ultraviolet radiation from said light source from reaching said control circuit substrate.

4. A deodorizer device according to claim 3, further comprising a stabilizer resistor for stabilizing operation of said ultraviolet lamp, and a power supply adapter for lowering a voltage of electrical power to be supplied to said ultraviolet lamp and to said stabilizer resistor, wherein use of said power supply adapter enables a size of said stabilizer resistor to be smaller than if said power supply adapter were not used.

5. A deodorizer device according to claim 3, further comprising a suction chamber and a discharge chamber separated from each other by said absorption unit, said suction chamber and said discharge chamber being provided with a suction opening and a discharge opening, respectively, said suction chamber accommodating said ultraviolet lamp with said reflection means.

6. A deodorizer device according to claim 5, wherein said control circuit substrate is disposed in said suction chamber, and wherein said control circuit substrate, said reflection means, said ultraviolet lamp, and said absorption unit are successively disposed within said suction chamber in an order of said control circuit substrate, said reflection means, said ultraviolet lamp, and said absorption unit.

7. A deodorizer device according to claim 6, wherein said stabilizer resistor is disposed in said discharge chamber, and wherein said ultraviolet lamp and said stabilizer resistor are positioned on opposite sides of said absorption unit.

8. A deodorizer device according to claim 7, wherein said control circuit substrate has means for hermetically sealing said circuit.

9. A deodorizer device according to claim 8, wherein said circuit includes heat generating elements capable of generating heat arranged on a lower side of said control circuit substrate, and wherein said circuit has terminals disposed in a vicinity of said heat generating elements.

10. A refrigerator deodorizer device for use in a refrigerator chamber which stores foods and other materials, comprising:
    an absorption unit including an odor absorbent capable of absorbing odor components in air and a layer of a photocatalyst deposited on a surface of said absorbent and operative to decompose said odor components absorbed by said absorbent when excited by irradiation with ultraviolet radiation;
    an ultraviolet lamp for irradiating said absorption unit with ultraviolet radiation;
    reflection means for reflecting said ultraviolet radiation from said ultraviolet lamp so as to direct said ultraviolet radiation towards said absorption unit;
    an ultraviolet lamp stabilizer for stabilizing operation of said ultraviolet lamp;
    a blower for directing air containing said odor components towards said absorption unit;
    a driving motor for driving said blower;
    a control circuit substrate carrying thereon an electrical circuit for controlling operation of said ultraviolet lamp and said driving motor; and
    housing means defining a suction chamber having a suction opening, and a discharge chamber having a discharge opening, said suction chamber and said discharge chamber being separated from each other by said absorption unit, said suction chamber accommodating said control circuit substrate, said reflection means, and said ultraviolet lamp, said discharge chamber accommodating said ultraviolet lamp stabilizer, said blower, and said driving motor.

11. A refrigerator deodorizer device according to claim 10, wherein said housing means has a height not greater than 100 mm so that said housing means can be installed in a space between adjacent shelves in a refrigerator chamber.

* * * * *